(12) United States Patent
Wang et al.

(10) Patent No.: US 8,030,289 B2
(45) Date of Patent: Oct. 4, 2011

(54) OLIGONUCLEOTIDE AND USE THEREOF

(75) Inventors: Liying Wang, Jilin province (CN); Dali Hu, Jilin province (CN); Ran Sun, Jilin province (CN); Yongli Yu, Jilin province (CN)

(73) Assignee: Changchun Huapu Biotechnology Co., Ltd., Changchun, Jilin (CN)

( * ) Notice: Subject to any disclaimer, the term of this patent is extended or adjusted under 35 U.S.C. 154(b) by 174 days.

(21) Appl. No.: 12/221,743

(22) Filed: Aug. 6, 2008

(65) Prior Publication Data
US 2010/0035972 A1 Feb. 11, 2010

(51) Int. Cl.
A61K 31/70 (2006.01)
C07H 21/02 (2006.01)
A01K 67/00 (2006.01)

(52) U.S. Cl. ........................................ 514/44; 536/23.1

(58) Field of Classification Search .................. None
See application file for complete search history.

(56) References Cited

U.S. PATENT DOCUMENTS
2007/0238678 A1* 10/2007 Barrat et al. .................... 514/44

FOREIGN PATENT DOCUMENTS
WO WO 2006/028742 3/2006

OTHER PUBLICATIONS

Sun et al. A human microsatellite DNA-mimicking oligodeoxynucleotide with CCT repeats negatively regulates TLR7/9-mediated innate immune responses via selected TLR pathways. Clin. Immunology 134:262-276, 2010.*
Barrat et al. Treatment of lupus-prone mice with a dual inhibitor of TLR7 and TLR9 leads to reduction of autoantibody production and amelioration of disease symptoms. Eur. J. Immunol. 37:3582-3586, 2007.*
Shirota et al. Suppressive oligodeoxynucleotides protect mice from lethal endotoxic shock. J. Immunology 174:4579-4583, 2005.*
Dong et al. Suppressive oligodeoxynucleotides delay the onset of glomerulonephritis and prolong survival in lupus-prone NZB x NZW mice. Arthritis & Rheumatism 52:651-658, 2005.*
Vallin, et al., Anti-Double-Stranded DNA Antibodies and Immunostimulatory Plasmid DNA in Combination Mimic the Endogenous IFN-α Inducer in Systemic Lupus Erythematosus, *The Journal of Immunology* 1999, 163:6306-6313.
Writing Committee of the World Health Organization, Avian Influenza A (H5N1) Infection in Humans, *New Eng. J. Med.*, 355;13 pp. 1374-1385 (2005).
DeWit, et al., Blood plasmacytoid dendritic cell response to CpG oligodeoxynucleotides are impaired in human newborns, *Blood*, 103:1030-1032 (2004).
Leadbetter et al., Chromatin-IgG complexes activate B cells by dual engagement of IgM and toll-like receptors, *Nature*, vol. 416:603-607 (2002).
Kumar et al., CpG Oligodeoxynucleotide and Montanide ISA 51 Adjuvant Combination Enhanced the Protective Efficacy of a Subunit Malaria Vaccine, *Infection and Immunity*, vol. 72, No. 2, pp. 949-957 (2004).
Slifka et al., Clinical implications of dysregulated cytokine production, *J. Mol. Med.*, 78:74-80 (2000).
Liew et al., Negative regulation of toll-like receptor-mediated immune responses, *Nature Reviews*, vol. 5, pp. 466-458 (2005).
Hochrein et al., Herpes simplex virus type-1 induces IFN-α production via toll-like receptor 9-dependent and-independent pathways, *PNAS*, vol. 101 pp. 11416-11421 (2004).
Duramad et al., Inhibitors of TLR-9 Act on Multiple Cell Subsets in Mouse and Man in Vitro and Prevent Death in Vivo from Systemic Inflammation, *The Journal of Immunology*, 2005, 174:5193-5200.
Barrat et al., Nucleic acids of mammalian origin can act as endogenous ligands for toll-like receptors and may promote systemic lupus erythematosus, *JEM*, vol. 202, No. 8, (2005) 1131-1139.
Vallin et al., Patients with systemic lupus erythematosus (SLE) have a circulating inducer of interferon-alpha (IFN-α) production acting on leucocytes resembling immature dendritic cells, *Clin Exp Immunol*, 1999, 111:196-202.
Espat et al., PEG-BP-30 Monotherapy attenuates the cytokine-mediated inflammatory cascade in baboon *Escherichia coli* septic shock, *Journal of Surgical Research*, 59, 153-158 (1995).
Ito et al., Specialization, kinetics, and repertoire of type 1 interferon responses by human plasmacytoid predendritic cells, *Blood*, (2006) vol. 107, No. 6.
Arthur M. Krieg, Therapeutic potential of toll-like receptor 9 activation, Nature Reviews, vol. 5, pp. 471-484 (2006).
Christensen et al., Toll-like receptor 7 and TLR9 dictate autoantibody specificity and have opposing inflammatory and regulatory roles in a murine model of lupus, *Immunity*, vol. 25:417-428 (2006).
Boulé et al., Toll-like receptor 9-dependent and -independent dendritic cell activation by chromatin-immunoglobulin G complexes, *J. Exp. Med.*, vol. 199, No. 12, (2004) pp. 1631-1640.
Marshall et al., *Toxoplasma gondii* Triggers Granulocyte-Dependent Cytokine-Mediated Lethal Shock in D-Galactosamine-Sensitized Mice, *Infection and Immunity*, vol. 66, No. 4 (1998) p. 1325-1333.
Hashem et al, Hybrid Oligomer Duplexes Formed with Phosphorothioate DNAs: CD Spectra and Melting Temperatures of S-DNA-RNA Hybrids are Sequence-Dependent but Consistent with Similar Heteronomous Conformations, *Biochemistry* 37, 61-72 (1998). XP-002970373.
Hung, et al., Evidence from CD spectra that d(purine) r(pyrimidine) and r(purine) d(pyrimidine) hybrids are in different structural classes, *Nucleic Acids Research*, vol. 22, No. 20 (1994). XP-002500581.

(Continued)

*Primary Examiner* — Quang Nguyen
(74) *Attorney, Agent, or Firm* — Cozen O'Connor

(57) ABSTRACT

An oligonucleotide with a nucleotide sequence of 5'-cctcctc-ctcctcctcctcctcct-3' (SEQ ID NO: 1) inhibits proliferation of human PBMC activated by TLR9 agonist and interferon production from human PBMC induced by TLR9 agonist, HSV-1, flu virus and serum from SLE patients, and rescues the mice from cytokine-mediated lethal shock. This oligonucleotide can be used as a remedy for the treatment of systemic lupus erythematosus (SLE), sepsis, multiple organ dysfunction syndromes and other immune-mediated disorders.

16 Claims, 5 Drawing Sheets

OTHER PUBLICATIONS

Ashman, et al., Sequence requirements for oligodeoxyribonucleotide inhibitory activity, *International Immunology*, vol. 17, No. 4, pp. 411-420. XP-002380605 •, 2005.

Mackay et al., Autoimmune Diseases, *The New England Journal of Medicine*, vol. 345 No. 5, pp. 340-350 (2001).

Dennis M. Klinman, Immunotherapeutic uses of CpG oligodeoxynucleotides, *Nature Reviews*, vol. 4, pp. 1-10 (2004).

Marcus E. Peter, ROS Eliminate Danger, *Immunity* 29, pp. 1-2 (2008).

Wang et al., The cytokine storm and factors determining the sequence and severity of organ dysfunction in multiple organ dysfunction syndrome, *American Journal of Emergency Medicine* (2008) 26, 711-715.

Wellmann et al., The evolution of human anti-double-stranded DNA autoantibodies, *PNAS*, (2005) vol. 102, No. 26, pp. 9258-9263.

Wang et al., Toll-like receptor-mediated activation of neutrophils by influenza A virus, *Blood*, Published online Jun. 10, 2008, pp. 130.

* cited by examiner

OLIGONUCLEOTIDE AND USE THEREOF

BACKGROUND OF THE INVENTION

1. Field of the Invention

The present invention relates to an oligonucleotide and a remedy for treating immune-mediated disorders, using the oligonucleotide. The immune-mediated disorder includes autoimmune disease, graft rejection, hypersensitivity, diseases associated with the over-stimulation of host's immune system by autoantigens, microbes and Toll-like receptor (TLR)-mediated disease.

2. Description of the Related Art

The present invention provides an oligonucleotide which has a nucleotide sequence of 5'-cctcctcctcctcctcctcctcct-3' (SEQ ID NO: 1) and a remedy for treating and/or preventing immune-mediated disorder, using the oligonucleotide.

The immune system protects human body from bacterial, parasitic, fungal, viral infections and from the growth of tumor cells. However, the immune response can sometimes be unwanted and cause immune-mediated disorder. The disorder includes autoimmune disease, graft rejection, hypersensitivity, diseases associated with the over-stimulation of host's immune system by microbes and Toll-like receptor (TLR)-mediated disease.

The autoimmune diseases results from an adaptive immune response and innate immune response or both against endogenous and/or exogenous antigens. Foreign substances, derived from bacteria, parasites, fungi or viruses, may mimic self-proteins and stimulate the immune system to launch responses to a self-cell and tissue, resulting in the diseases including but not limited to systemic lupus erythematosus ☐SLE☐ and rheumatoid arthritis. The graft rejection is a consequence of organ or tissue transplantation caused by the immune response in the transplant recipient (host) to the transplanted organ/tissue. When a subject is transplanted with grafts including kidney, pancrea, heart, lung, bone marrow, cornea and skin, the subject can launch an immune response (rejection) against the grafts. Hypersensitivity is an inappropriate immune response that has deleterious effects, resulting in significant tissue damage or even death. The hypersensitivity is divided into four types (e.g. Types I, II, II and IV. Disease associated with the over-stimulation of host's immune system by microbes is triggered by the infection of viruses such as flu viruses and other microbes. In the case of flu virus and Gram-negative bacterial infection, an excessive immune response to the invaders appears to be a fatal factor in patients. The response is characterized by the overproduction of cytokines. Studies of septic shock syndrome demonstrate that over production/aberrant production of cytokines can lead to rapid mortality due to cytokine-mediated lethal shock (Slifka M K, et al. J Mol Med. 2000; 78(2):74-80). Septic shock following gram-negative infection is a leading cause of mortality in critically ill patients. The exaggerated production of cytokines is known to contribute to sepsis characterized by cytokine-mediated lethal shock (Espat N J, et al. J Surg Res. 1995 July; 59 (1):153-8). Multiple organ dysfunction syndromes (MODS) are a major cause of morbidity and mortality in severe sepsis and shock. Cytokine-mediated lethal shock resulted from over-production of host cytokines is considered a main mechanism leading to MODS (Wang H, et al. Am J Emerg Med. 2008 July; 26 (6):711-5). Toll-like receptor (TLR)-mediated disease is a disorder caused by the activation of Toll like receptors (TLRs). TLRs are a family of receptors that recognize microbe derived molecular structures (pathogen-associated molecular patterns or PAMPs). TLR expressing immune cells are activated upon binding of PAMPs. TLRs recognize a range of pathogen-derived products and activated. Lipopolysaccharide (LPS) of bacteria recognized by TLR4, lipotechoic acid and diacylated lipopeptides by TLR2-TLR6 dimmer, triacylated lipopeptides by TLR2-TLR1 dimmer, CpG containing oligonucleotide (CpG ODN) synthesized or derived from either viruses or bacteria by TLR9, bacterial flagellin by TLR5, zymosan by TLR2-TLR6 dimmer, F protein from respiratory syncytial virus (RSV) by TLR4, viral-derived double-stranded RNA (dsRNA) and poly I:C, a synthetic analog of dsRNA by TLR3; viral DNA by TLR9, single-stranded viral RNA (VSV and flu virus) by TLR7 and TLR8 (Foo Y. Liew, et al. Nature Reviews Immunology. Vol 5, June 2005, 446-458). In recent years, TLR activation has been connected to the pathogenesis of some of diseases including sepsis, dilated cardiomyopathy, diabetes, experimental autoimmune encephalomyelitis, systemic lupus erythematosus, atherosclerosis, asthma, chronic obstructive pulmonary disease and organ failure (Foo Y. Liew, et al. Nature Review Immunology, Vol 5, 2005, 446-458). Activation of TLR9 by self DNA play an important role in the development of autoimmune diseases such as SLE (Christensen S R, et al. Immunity 2006; 25:417-28) and rheumatoid arthritis (Leadbetter E A, et al. Nature 2002; 416:603-7; Boule M W, et al. J Exp Med 2004; 199:1631-40). Moreover, the elevated production of interferons (IFNs) resulted from TLR-9 activation has been reported to contribute to the develop of systemic lupus erythematosus (Barrat F J, et al. J Exp Med 2005; 202:1131-9; Wellmann U, et al. Proc Natl Acad Sci USA 2005; 102:9258-63).

In this invention, we disclose an oligonucleotide with a nucleotide sequence of 5'-cctcctcctcctcctcctcctcct-3' (SEQ ID NO: 1) that inhibits proliferation of human PBMC activated by TLR9 agonist, inhibits interferon production from human PBMC induced by TLR9 agonist, HSV-1, flu virus and serum from SLE patients, and rescues the mice from cytokine induced shock. Therefore, this oligonucleotide is useful as a remedy for the treatment immune-mediated disorders.

The oligonucleotides of the invention inhibits TLR9 activation. It has been documented that TLR9 agonist activates both innate and adaptive immune response (Arthur M. Krieg. Nature Reviews Drug Discovery, Vol 5. June 2006, 471-484). CpG containing oligonucleotides (CpG ODN) is a TLR9 agonist [D. M. Klinman, Nat. Rev., Immunol. 4 (2004) 249-258]. The oligonucleotides of the invention inhibits the proliferation and interferon production of human PBMC stimulated by CpG ODN, indicating that the oligonucleotide of the invention can be used as a remedy for the treatment of diseases related to TLR9 activation. Because TLR9 activation has been reported to contribute to the development of SLE (Barrat F J, et al. J Exp Med 2005; 202:1131-9; Wellmann U, et al. Proc Natl Acad Sci USA 2005; 102:9258-63; Christensen S R, et al. Immunity 2006; 25:417-28) and rheumatoid arthritis (Leadbetter E A, et al. Nature 2002; 416:603-7; Boule M W, et al. J Exp Med 2004; 199:1631-40), the oligonucleotide of the invention can be used as a remedy for the treatment of SLE and rheumatoid arthritis by inhibiting the TLR9 activation.

The oligonucleotide of the invention inhibits the interferon production from human PBMC induced by TLR9 agonist, HSV-1, flu virus and serum from SLE patients. Because the elevated production of interferons has been reported to contribute to the development of SLE (Barrat F J, et al. J Exp Med 2005; 202:1131-9; Wellmann U, et al. Proc Natl Acad Sci USA 2005; 102:9258-63), the oligonucleotide of the invention can be used as a remedy for the treatment of SLE by inhibiting IFN production.

The oligonucleotides of the invention inhibits the interferon production from human PBMC induced by flu virus (PR8). Since influenza virus has been documented to be able to activate TLR7 and TLR8 (Wang J P, et al. Blood. 2008 Jun. 10. [Epub ahead of print]), the oligonucleotide of the invention can be used as a remedy for the treatment of Toll-like receptor (TLR)-mediated disease by inhibiting TLR7 or TLR8.

The oligonucleotides of the invention inhibits the interferon production from human PBMC induced by HSV-1. Since HSV-1 has been documented to activate TLR9 (Hubertus Hochrein et al. PNAS, 101, 11416-11421), the oligonucleotide of the invention can be used as a remedy for the treatment of Toll-like receptor (TLR)-mediated diseases including but not limited to SLE by inhibiting the activation of TLR9.

To study in vivo activity of the oligonucleotide of the invention, a mouse model of cytokine-mediated lethal shock was used. The mouse model was created by injecting CpG ODN into the D-galactosamine (D-Gal) presensentised mice. After being crated, the model mice died within 12 to 24 h. Analyses of plasma cytokines revealed over-production of tumor necrosis factor (TNF) alpha and interleukin-12 (IL-12) and gamma interferon (IFN-gamma) (Marshall A J, et al. Infect Immun. 1998 April; 66(4):1325-33; Peter M, Bode K, et al. Immunology. 2008 January; 123(1):118-28). By using the model, we demonstrate that the oligonucleotide of the invention can rescue mice from cytokine-mediated lethal shock. Because the cytokine-mediated lethal shock contributes to the septic shock (Slifka M K, et al. J Mol. Med. 2000; 78(2):74-80; Espat N J, et al. J Surg Res. 1995 July; 59(1): 153-8) and multiple organ dysfunction syndromes (MODS) (Wang H, et al. Am J Emerg Med. 2008 July; 26(6):711-5), the oligonucleotide of the invention can be used as a remedy for the treatment of sepsis and MOGS by rescuing the host from cytokine-mediated lethal shock.

SUMMARY OF THE INVENTION

In the first embodiment, the present invention provides an oligonucleotide with a nucleotide sequence of 5'-cctcctcctc-ctcctcctcctcct-3' (SEQ ID NO: 1) and the oligonucleotides that fit the formula of (5' CCT 3') n.

In the second embodiment, the present invention provides a remedy for treating immune-mediated disorder using the oligonucleotide of the invention. The immune-mediated disorder includes autoimmune disease, graft rejection, hypersensitivity, diseases associated with the over-stimulation by of host's immune system by autoantigens, microbes and Toll-like receptor (TLR)-mediated disease.

In the third embodiment, the present invention provides a remedy for treating immune-mediated disorder using the oligonucleotides of the invention by inhibiting the TLR activation and IFN production induced by DNA virus, RNA virus, the serum from SLE patients, and by rescuing a subject from cytokine-mediated lethal shock.

In the fourth embodiment, the present invention provides a remedy for treating SLE, sepsis and multiple organ dysfunction syndromes in a subject using the oligonucleotides of the invention.

In the fifth embodiment, the present invention provides a remedy for treating immune-mediated disorder by administering the oligonucleotide of the invention alone or with a pharmaceutically acceptable carrier to a subject through the route of enteral, parenteral and topical administration or inhalation.

In the sixth embodiment, the present invention provides a composition comprising therapeutically effective amount of the oligonucleotides of the invention for the treatment of immune-mediated disorder.

In another embodiment, the present invention provides a remedy for the treatment of immune-mediated disorder by administering the oligonucleotides of the invention alone or in combination with additional active ingredients.

In another embodiment, the present invention provides a remedy for the treatment of immune-mediated disorder by administering the oligonucleotide of the invention in delivery vehicles.

Thereby, in a aspect, the present invention provides the oligonucleotide includes a sequence that fits the formula of (5' CCT 3') n (SEQ ID NO: 2), wherein 5' CCT 3' is a repeat unit and n is an integer from 2 to 50, preferably, it is 5'-cctcctc-ctcctcctcctcct-3' (SEQ ID NO: 1).

In a preferable embodiment, the phosphate backbone of the oligonucleotide can be partly or completely phosphorothioate-modified, or unmodified.

In another preferable embodiment, the oligonucleotide can be developed into their derivatives by adding in one or several nucleotides to each end of the oligonucleotide and by changing one or several bases in the oligonucleotide.

In another preferable embodiment, the oligonucleotide constitutes a part of other DNA molecules, plasmid or viral vectors.

In an even more preferable embodiment, the oligonucleotide can undergo chemical modification.

In another aspect, the present invention provides a method for treating an immune-mediated disorder in a subject comprising administrating the subject with above oligonucleotide. Preferably, the immune-mediated disorder is autoimmune disease, or hypersensitivity, or graft rejection, or disease associated with the over-stimulation of host's immune system by microbes or Toll-like receptor (TLR)-mediated disease.

In a preferable embodiment, the subject is a human or non-human vertebrate.

In a more preferable embodiment, the treatment of an immune-mediated disorder is carried out by a mechanism selected from the group comprising inhibiting the proliferation of immune cells activated with Toll like receptor 9 agonist, inhibiting the activation of Toll like receptor 9, inhibiting interferon production, and rescuing a subject from cytokine-mediated lethal shock.

In a more preferable embodiment, the immune-mediated disorder is systemic lupus erythematosus (SLE) which is treated by inhibiting TLR9 activation and interferon production induced by TLR9 agonists, viruses and the serum of SLE patient, the immune-mediated disorder is sepsis which is treated by rescuing a subject from cytokine-mediated lethal shock, or the immune-mediated disorder is multiple organ dysfunction syndromes which is treated by rescuing a subject from cytokine-mediated lethal shock.

In another aspect, the present invention provides a remedy for administrating to a subject having or at risk of developing the immune-mediated disorder comprising above oligonucleotide. Preferably, the remedy further comprises a pharmaceutically acceptable carrier and/or additional active ingredients. More preferably, the remedy is in a form for administrating through the route including the enteral, parenteral and topical administration or inhalation.

In another embodiment, the oligonucleotide can be pegylated.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

Data from one representative experiment of three are shown. HSV-1 represents herpes simplex virus-type 1 virus. PR8 represents flu virus ($H1N_1/PR8$).

Figure 4:
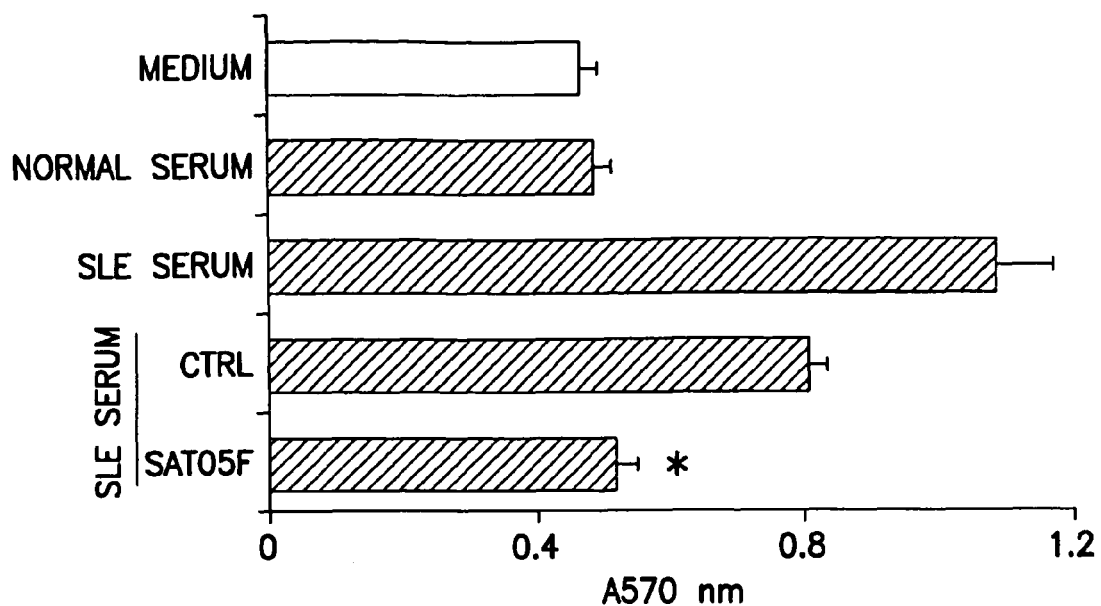

FIG. 4 is a graph showing that SAT05F inhibits interferon production of from hPBMCs stimulated with serum of SLE patients.

Figure 5:
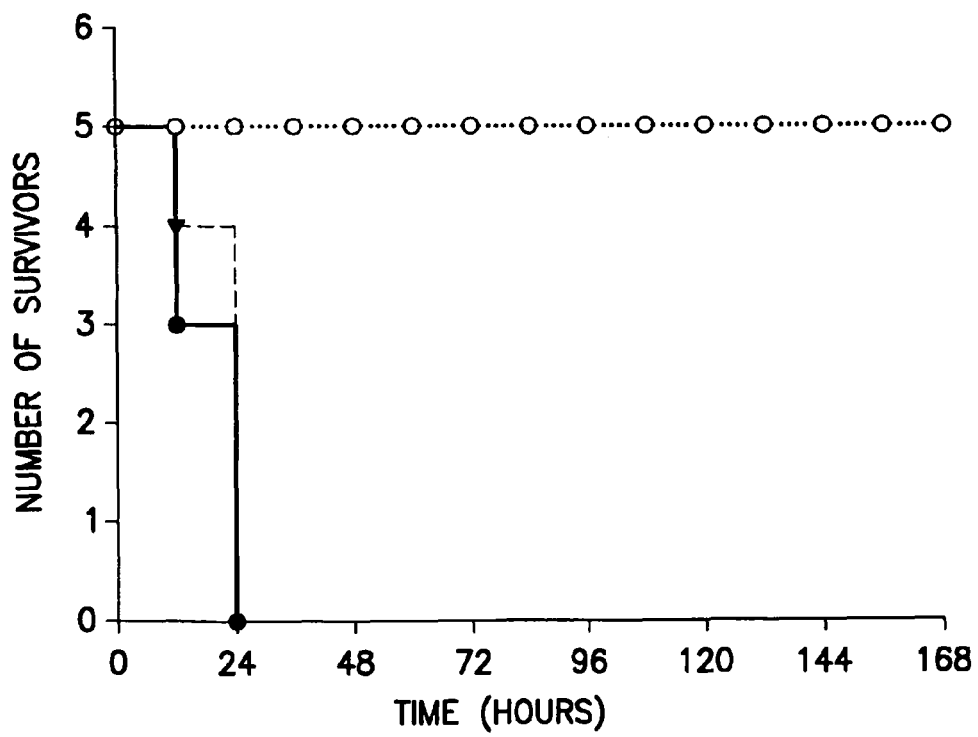

FIG. 5 is a graph showing that SAT05F rescues mice from cytokine-mediated lethal shock.

EXAMPLES

The invention will now be described in more detail in the following Examples. But the invention is not limited to these Examples. In these Examples, herein, experiments using commercially available kits and reagents were done according to attached protocols, unless otherwise stated. The skilled artisan will appreciate that the oligonucleotides of the present invention can easily be applied to treat an immune-mediated disorder. The present invention will now be demonstrated by the following non-limiting examples. All reagents used to manipulate the oligonucleotides (ODNs) in the following examples were pyrogen-free. The endotoxin in the ODN preparations was tested by using the *Limulus amebocyte* lysate assay (Associates of Cape Cod, Inc).

Human PBMCs (hPBMC), used in the following samples, were isolated from buffy coats (The Blood Center of Jilin Province, China) by Ficoll-Hypaque (Pharmacia) density gradient centrifugation (P. M. Daftarian et al., (1996): Journal of Immunology, 157, 12-20). The cells were cultured in IMDM supplemented with 10% (v/v) heat-inactivated fetal bovine serum (FBS; GIBCO) and antibiotics (100 IU of penicillin/ml and 100 IU of streptomycin/ml) at 37° C. in a 5% $CO_2$ humidified incubator. The viability of the cells was 95-99% as determined by trypan blue exclusion.

Example 1

Effect of SAT05f on CpGODN Induced Proliferation of Human PBMC

The oligonucleotides (ODNs) used in the example were synthesized in Sangon Biotech Company (Shanghai, China) and were CpG2006 (5'-tcgtcgttttgtcgttttgtcgtt-3' (SEQ ID NO: 3)), CpG C274 (5'-tcgtcgaacgttcgagatgat 3' (SEQ ID NO: 4)), A151 (5'-ttagggttagggttagggttaggg-3' (SEQ ID NO: 5)) (Hidekazu Shirota, et al. The Journal of Immunology, 2005, 174: 4579-4583), SAT05f (5'-cctcctcctcctcctcctcctcct-3' (SEQ ID NO: 1)) and Control ODN (5'-gttagagattaggca-3' (SEQ ID NO: 6)).

CpG2006 (Dominique De Wit, et al. Blood, 2004, Vol 103, Num 3:1030-103) is a prototype of B-type CpG ODN. CpG C274 (Omar Duramad, et al. The Journal of Immunology, 2005, 174: 5193-5200) is a prototype of C type CpG ODN.

[$^3$H] thymidine incorporation assay was used to test whether SAT05f inhibited the proliferation of hPBMC stimulated by CpG2006 or CpG C274. Briefly, hPBMCs ($5 \times 10^5$/well) were plated in 96-well U-bottomed plates (Costar) and cultured with CpG2006 (1 μg/ml) or CpG C274 (1 μg/ml) in the presence of SAT05f or A151 or Control ODN for 48 h, followed by pulsing with [$^3$H] thymidine (New England Nuclear, Boston, Mass.) for 16 h. The cells were harvested on glass fiber filters and detected in a scintillation counter. The cell proliferation in triplet wells was expressed as mean cpm (counts per minute)±SD.

Figure 1:
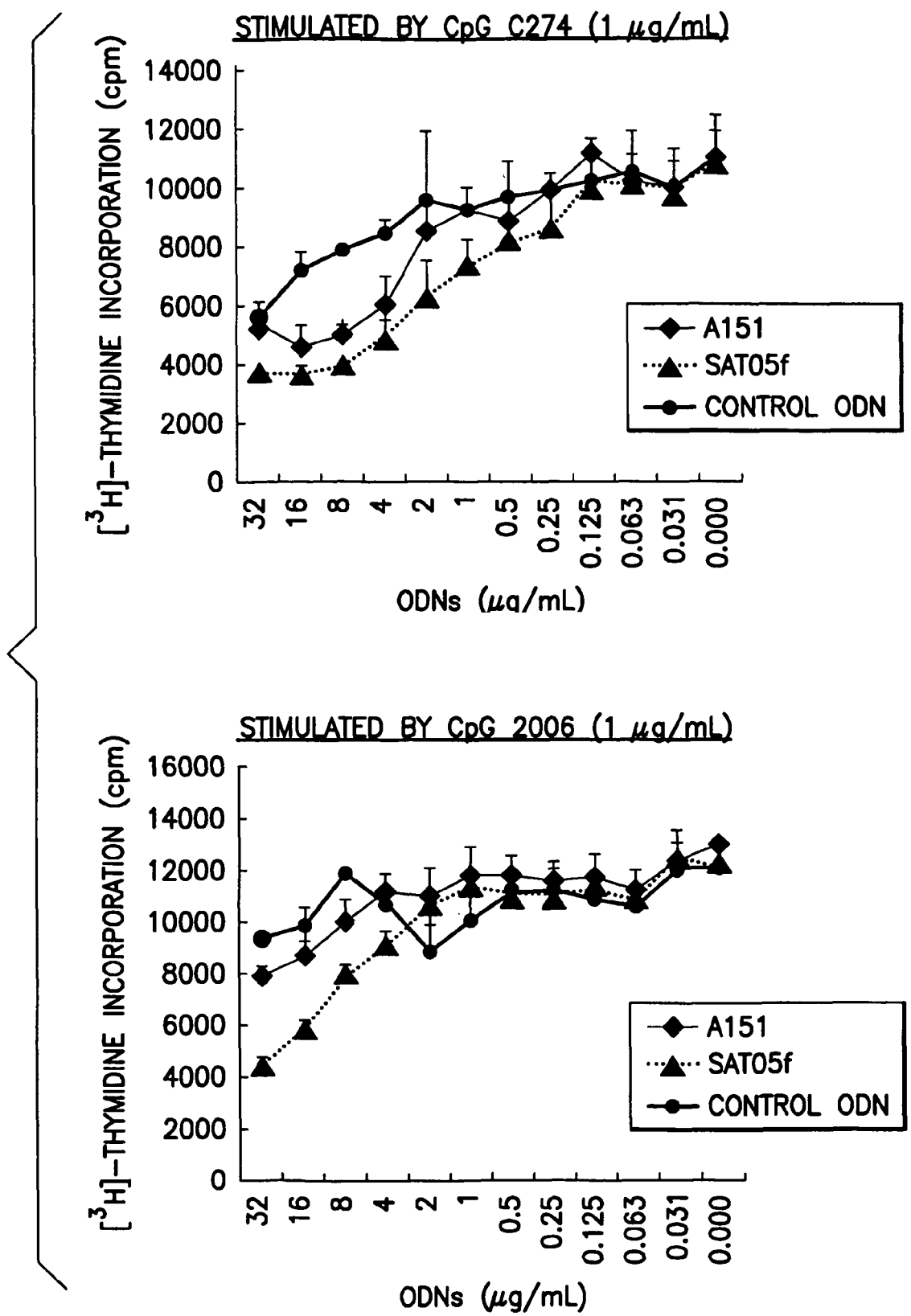
FIG. 1 shows graphs depicting the inhibition of SAT05f on the proliferation of human PBMC stimulated by CpG 2006 and CpG C274.

As shown in FIG. 1, SAT05f inhibits the proliferation of hPBMCs stimulated with CpG ODN 2006 or CpG ODN C274. The inhibitory effect is stronger than that induced by A151. Control ODN can not induce the inhibition. Since CpG ODN including CpG2006 or CpG C274 is a TLR9 agonist [D. M. Klinman, Nat. Rev., Immunol. 4 (2004) 249-258], the data indicate that SAT05f inhibits TLR9 activation and can be used to treat the diseases related to TLR9 activation and other Toll-like receptor (TLR)-mediated diseases.

Example 2

Effect of SAT05f on CpGODN-Induced Interferon Production from Human PBMC

<Experimental Method>

Vero E6 cells (African green monkey kidney cell line, American Type Culture Collection) were cultured at 37° C. in a 5% CO2 humidified incubator and maintained in IMDM supplemented with 10% (v/v) heat-inactivated fetal bovine serum (FBS; GIBCO) and antibiotics (100 IU of penicillin/ml and 100 IU of streptomycin/ml).

An interferon (IFN) bioassay using Vero E6 cells and VSV was performed to test whether SAT05f inhibited the IFN production from hPBMC stimulated by CpG C274. The ODNs including CpG C274, A151, SAT05f and Control ODN were synthesized in Sangon Biotech Company (Shanghai, China). The sequences of CpG C274, A151, SAT05f and Control ODN are indicated as in example 1. CpG C274 is a prototype of C type CpG ODN and shares the activities of both A type CpG ODN and B type CpG ODN. A-type CpG ODN and capable of activating human plasmacytoid dendritic cells (pDCs) to produce large amount of type I interferon. hPBMCs ($5 \times 10^5$/well) were plated in 96-well U-bottomed plates (Costar) and cultured with CpG C274 (1 μg/ml) in the presence of SAT05f or A151 or Control ODN for 48 h and the supernatants were then collected for assaying their IFN activity. Vero E6 cells ($3 \times 10^4$/well) were seeded into 96-well flat-bottomed plates and cultured for 24 h to confluence. The cells were then incubated with 100 µl of the supernatants for 18 h and then challenged with 10×TCID50 (50% tissue culture infectious doses) of VSV for another 48 h. Vesicular stomatitis virus (VSV) was grown in Vero E6 cells. After titration, the virus was stored in aliquots at −70° C. until use. After staining with 0.5% crystal violet, the cytopathic effect of virus was examined using Multi-well Microtiter Plate Reader at A578 nm and expressed as OD values.

<Experimental Results>

Figure 2:
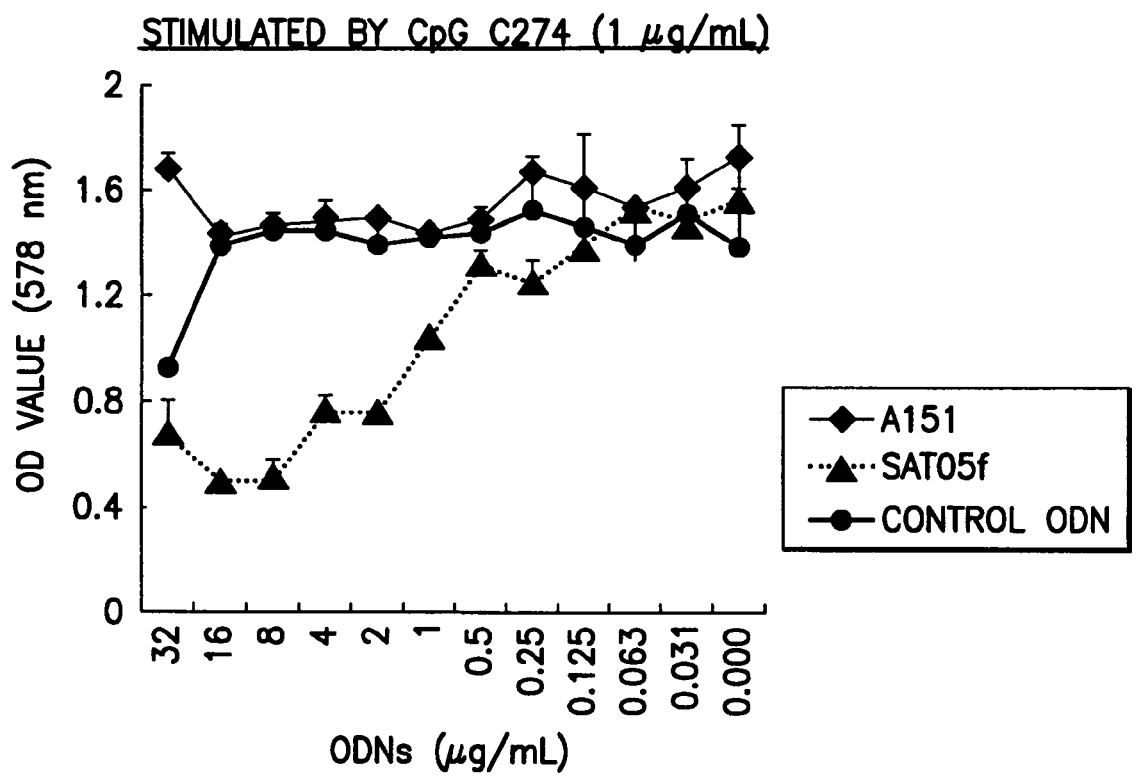
FIG. 2 shows a graph depicting the inhibition of SAT05f on interferon production from human PBMC stimulated by CpG C274.
Figure 3A:
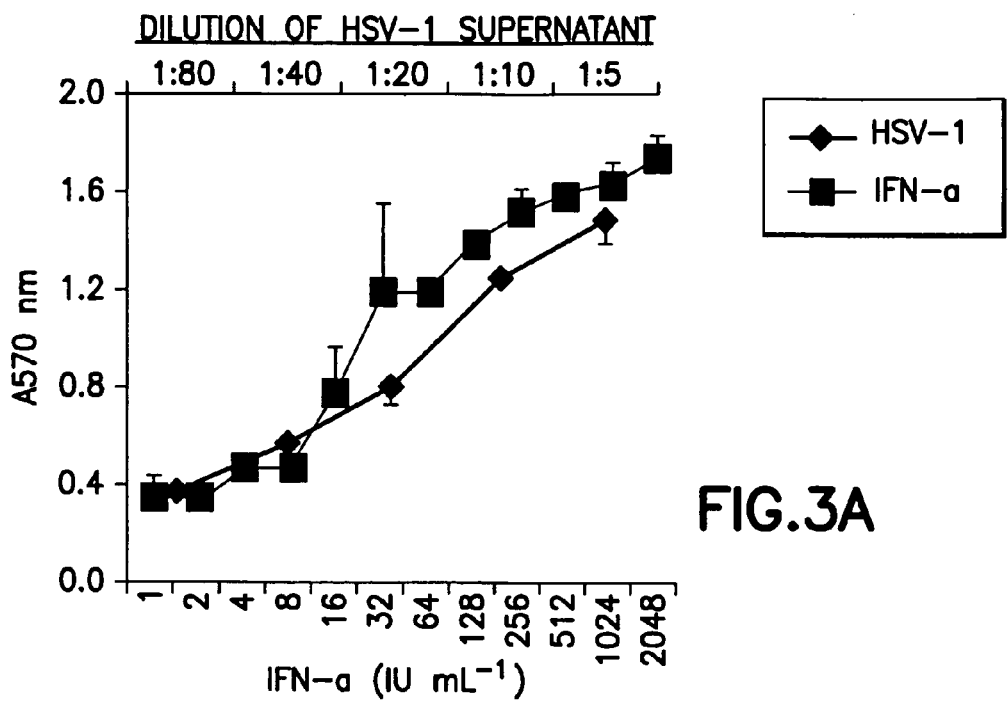
FIG. 3 shows graphs depicting the inhibition of SAT05f on interferon production from human PBMCs stimulated with herpes simplex virus-type 1 virus and flu virus (A) Comparison of the anti-viral activity between the interferon (IFN) induced by inactivated HSV-1 and recombinant human interferon (IFN)-α. 'IU' represents the international unit. (B) Inhibitory effect of SAT05F on IFN production from human PBMC (hPBMC) stimulated by inactivated HSV-1. (C) The dose effect of SAT05F on IFN production from human PBMCs stimulated by HSV-1. (D) Comparison of the anti-viral activity between the interferon (IFN) induced by inactivated PR8 and recombinant human interferon (IFN)-α. (E) Inhibitory effect of SAT05F on IFN production from hPBMC stimulated with inactivated PR8. (F) The dose effect of SAT05F on IFN production from hPBMC stimulated with inactivated PR8.
Figure 3B:
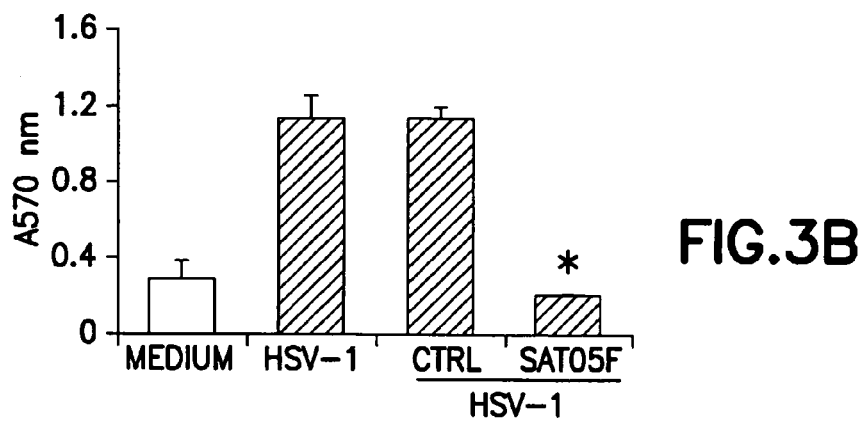
Figure 3C:
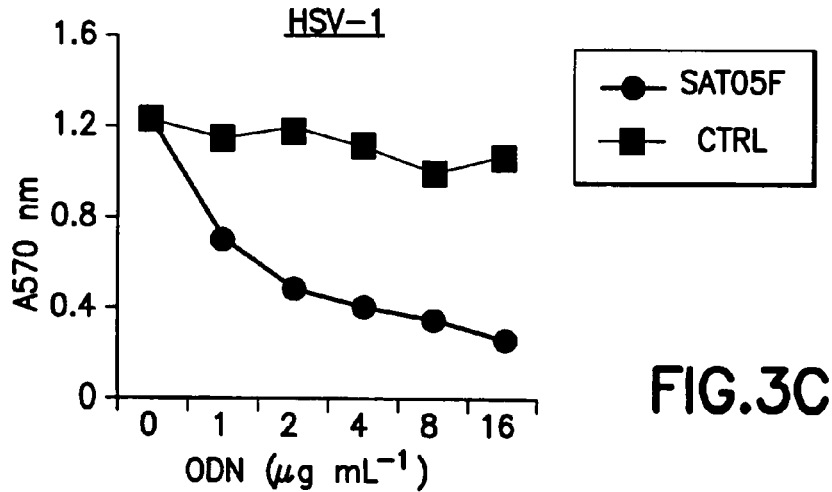
Figure 3D:
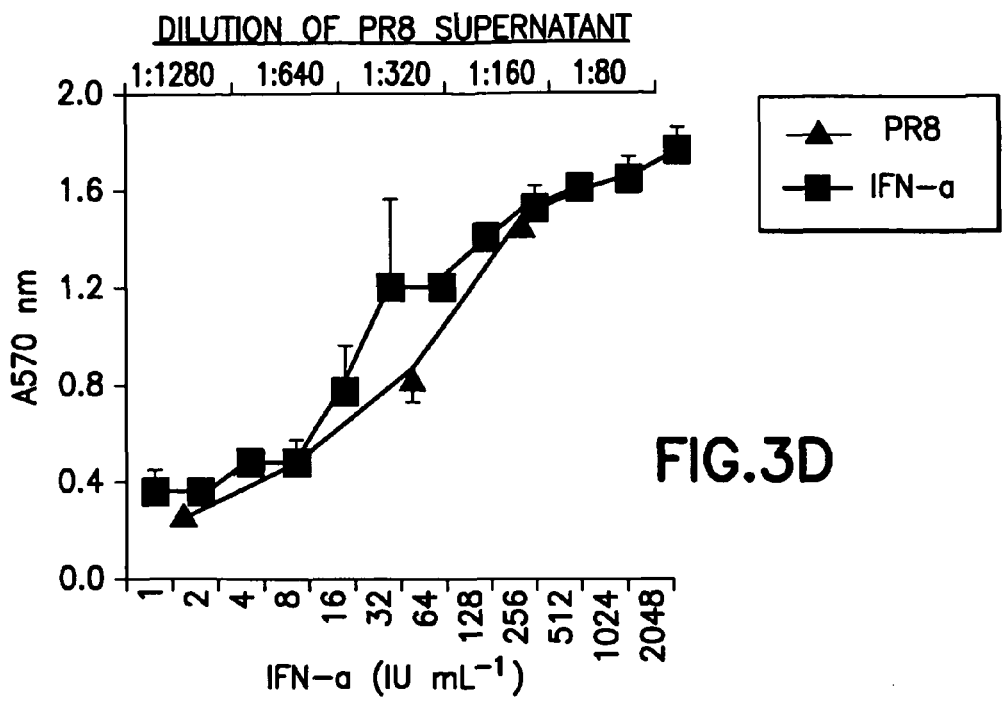
Figure 3E:
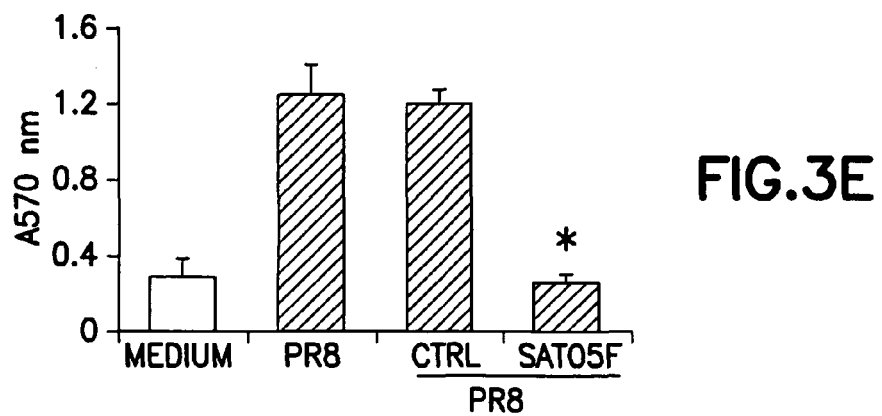
Figure 3F:
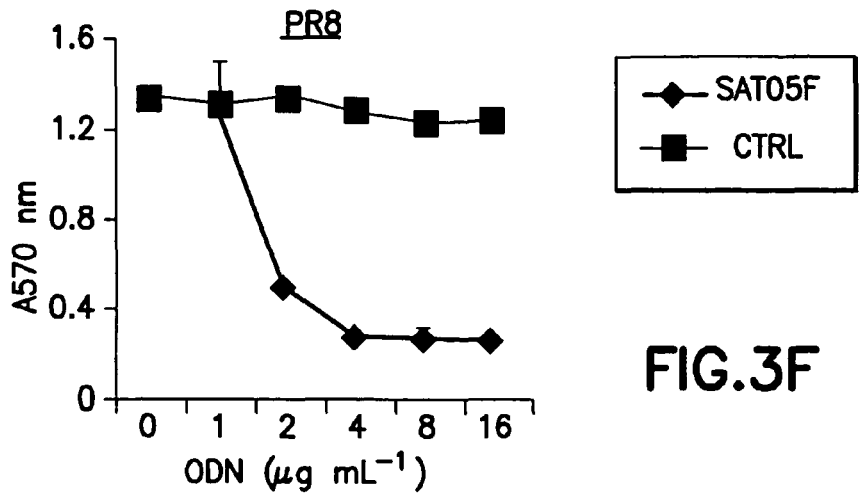

As shown in FIG. 2, SAT05f inhibits IFN production from hPBMC stimulated with CpG C274. Since elevated production of IFNs resulted from TLR-9 activation has been reported to contribute to the developing systemic lupus erythematosus (SLE) (Barrat F J, et al. J Exp Med 2005; 202:1131-9; Wellmann U, et al. Proc Natl Acad Sci USA 2005; 102:9258-63), the data indicate that SAT05f can be used as a remedy to treat SLE and other Toll-like receptor (TLR)-mediated diseases by inhibiting elevated IFN production.

Example 3

Inhibitory Effect of SAT05F on Interferon Production from Human PBMCs Stimulated with Herpes Simplex Virus-Type 1 and Flu Virus <Experimental Method>

Vero E6 cells were cultured as described in example 2. HSV-1 (herpes simplex virus-type 1) and PR8 (H1N1/PR8, a lab used flu virus) were originally obtained from Department of Immunology, Medical College of Norman Bethune, Jilin University, Changchun. HSV-1 (MOI=200) was propagated on Vero E6 cells and PR8 (MOI=3) was propagated on MDCK cells (Madin-Darby Canine Kidney Cells, ATCC). The MDCK cells were maintained in IMDM supplemented with 10% (v/v) heat-inactivated fetal bovine serum (FBS; GIBCO) and antibiotics (100 IU of penicillin/ml and 100 IU of streptomycin/ml). HSV-1 in IMDM supplemented with 2% (v/v) FBS was inactivated by heating at 70° C. in a water bath for 10 min and PR8 in IMDM supplemented with 2% (v/v) FBS was inactivated by heating at 56° C. in a water bath for 30 min.

The ODNs including SAT05F and CTRLODN □indicated as CTRL in the FIG. 3□ with nucleotide sequence of 5'-aaaaataaaaataaaataaaat-3' (SEQ ID NO: 7) were synthesized by Takara Co (Dalian, China). The sequence of SAT05F is indicated as in the example 1.

hPBMCs ($5\times10^6$/ml) were cultured in 96 well plate with inactivated HSV-1 or inactivated PR8 in the absence or presence of SAT05F or control ODN (CTRL ODN) at 37° C. for 48 h. The supernatants were then collected for assaying. The Vero E6 cells were seeded into 96-well flat-bottomed plates ($3\times10^4$/well) and cultured for 24 h to confluence. The cells were incubated with 100 μl of the diluted supernatants (1:20 diluted for the HSV-1 induced and 1:80 diluted for the PR8 induced) for 16 h and then challenged with 10×TCID50 (50% tissue culture infectious doses) of VSV for another 48 h. After staining with 0.5% crystal violet, the cytopathic effects were examined using Multi-well Microtiter Plate Reader at A570 nm and expressed as mean OD value±SD. Data from one representative experiment of three are shown.

<Experimental Results>

As shown in FIG. 3-A, inactivated HSV-1 virus could induced IFN that protected the Vero E6 cells from VSV attacking as recombinant human interferon IFN-αdid. As shown in FIG. 3-B, SAT05F inhibited IFN production from human PBMC (hPBMC) stimulated by inactivated HSV-1 virus. Dose effect analysis revealed that SAT05F could significant IFN production from human PBMC stimulated with inactivated HSV-1 in a dose dependent way. SAT05F at 1 μg/ml is efficient to mediate the inhibition (FIG. 3-C). As shown in FIG. 3-D, inactivated flu virus (PR8) could induced IFN efficient to protect the Vero E6 cells from VSV attacking as recombinant human interferon (IFN)-αdid. As shown in FIG. 3-E, SAT05F inhibited interferon (IFN) production from human PBMC (hPBMC) stimulated by inactivated flu virus (PR8). Dose effect analysis revealed that SAT05F at 2 μg/ml was efficient to inhibit the IFN production from hPBMC stimulated with inactivated PR8 and the inhibition reaches the maximum when SAT05F was used at 4 μg/ml (FIG. 3-F).

It has been demonstrated that flu virus recognizes and activates TLR7 (Wang J P, et al. Blood. 2008 Jun. 10. [Epub ahead of print]), and that HSV-1 recognizes and activates TLR9 (Hubertus Hochrein et al. PNAS, 101, 11416-11421), stimulating the production of IFN. Together with the results of the example, the oligonucleotides of the invention can be used as a remedy for the treatment of Toll-like receptor (TLR)-mediated disease such as SLE by inhibiting TLR7 or TLR9 activation and IFN production induced by virus.

Example 4

The Inhibitory Effect of SAT05F on Interferon Production of from hPBMCs Stimulated with Serum of SLE Patients <Experimental Method>

Anti-dsDNA-positive sera of SLE patients were obtained from Department of Rheumatology, China-Japan Union Hospital, Jilin University. ODNs including SAT05F and CTRL-ODN □indicated as CTRL in the FIG. 4□ with the sequence of 5'-AAAAATAAAAATAAAATAAAAT-3' (SEQ ID NO: 7) were synthesized by Takara Co (Dalian, China). The sequence of SAT05F is indicated as in example 1.

hPBMCs ($5\times10^6$/ml) were cultured in 96 well plate with 1:1 diluted anti-dsDNA-positive serum of SLE patient in the absence or presence of SAT05F or CTRL ODN for 48 h. hPBMCs incubated with medium alone or with anti-dsDNA-negative serum of healthy blood donor were set as controls. The supernatants were collected for assaying their IFN activity. The Vero cells were incubated with the collected supernatant (1:5 diluted) for 16 h. and then attacked by 10TCID50 of VSV for 48 h. After staining with 0.5% crystal violet, the cytopathic effects were examined using a multi-well microtiter plate reader at A570 nm.

<Experimental Results>

As indicated in FIG. 4, the serum from SLE patient stimulates IFN production from hPBMC, and SAT05F inhibits the IFN production from human PBMC stimulated with the serum from SLE patient. Data from one representative experiment of three are shown. It is well established that elevated production of IFNs contributes to the development of SLE (Barrat F J, et al. J Exp Med 2005; 202:1131-9; Wellmann U, et al. Proc Natl Acad Sci USA 2005; 102:9258-63). It has been demonstrated that endogenous IFN inducing factors has been reported existed in the serum of SLE patient (Kwok S K, et al. Arthritis Res Ther. 2008; 10(2):R29), SLE patients have a circulating inducer of IFN production, sera from SLE patient frequently induce the production of IFN in cultures of PBMC from healthy blood donors (Vallin H, et al Clin Exp Immunol. 1999 January; 115 (1):196-202), and that anti-double-stranded DNA antibodies or DNA-anti-DNA Ab complexes functions as endogenous IFN-alpha inducers in SLE patient and contribute to the pathogenesis of SLE (Vallin H, et al. J. Immunol. 1999 Dec. 1; 163(11):6306-13). Together, the data indicate that SAT05F can be used for the treatment of SLE patients by inhibiting IFN production, Example 5

The effect of SAT05F on Rescuing Mice from Cytokine-Mediated Lethal Shock

<Experimental Method>

In order to elucidate the in vivo functions of SAT05F, a model of cytokine-mediated lethal shock was induced with the reference of a general method (Peter M, et al. Immunology. 2008 January; 123(1):118-28; Marshall A J, et al. Infect Immun. 1998 April; 66(4): 1325-33).

Female BALB/C mice (20±1 g weight) obtained from the Experimental Animal Center, Medical College of Norman Bethune, Jilin University) were given free access to food and water during the experiment. The experiments were in accordance with local legislation.

Oligonucleotides including SAT05F with the sequence of 5'-cctcctcctcctcctcctcctcct-3' (SEQ ID NO: 1), CTRL-ODN with the sequence of 5'-aaaaataaaaataaaataaaat-3' (SEQ ID NO: 7) and CpG-ODN 1826 (1826) with the sequence of 5'-tccatgacgttcctgacgtt-3' (SEQ ID NO: 8)[Sanjai Kumar, et al. Infection and Immunity, February 2004, p. 949-957, Vol. 72, No. 2] were synthesized by Takara Co (Dalian, China).

D-galactosamin (D-(+)-Galactosamine HCL, D-GALN) was from DeBioChem, Nanjing, China.

The BALB/C mice, five in each group, were divided into groups of D-GALN+1826, D-GALN+1826+SAT05F, D-GALN+1826+CTRL-ODN. The mice were injected intraperitoneally (i.p.) with 500 μl of D-galactosamin (32 mg/ml in PBS). 1.5 h later, the mice were intraperitoneally (i.p.) injected with 1826 (10 μg/per mouse in PBS) and subsequently injected (i.p.) with 50 μg of SAT05F (in PBS) (in D-GALN+1826+SAT05F group) or CTRL-ODN (in D-GALN+1826+CTRL-ODN group). In D-GALN+1826 group, the mice were injected with D-galactosamin and 1826 only. The mice were monitored and lethality was recorded.

<Experimental Results>

As indicated in FIG. 5, in the D-GALN+1826 group or D-GALN+1826+CTRL-ODN group of the model, all of the five mice were deprived of life in 24 after the D-galactosamin injection, Comparatively, in 168 hours after the D-galactosamin injection, all of five mice in D-GALN+1826+ SAT05F group survived, demonstrating that SAT05F can rescue the mice received D-galactosamin and 1826. It was documented that D-galactosamin presensitized mice could be created into cytokine-mediated lethal shock animal models by injecting CpG OD (Peter M, et al. Immunology. 2008 January; 123(1):118-28). As apparently shown in these results, the data indicate that SAT05F is suppressive in vivo and inhibits cytokine-mediated lethal shock. Data from one representative experiment of two are shown.

DETAILED DESCRIPTION OF THE PRESENTLY PREFERRED EMBODIMENTS

Unless otherwise noted, all terms in the invention have the same meaning as commonly understood by one of ordinary skill in the art to which this disclosure belongs. The singular terms "a," "an," and "the" include plural referents unless context indicates otherwise. Similarly, the word "or" is intended to include "and" unless the context indicates otherwise. In case of conflict, the present specification, including explanations of terms, will control. In addition, the materials, methods and examples are illustrative only and not intended to be limiting. Treat, treating or treatment shall have the same meaning without concerning the grammar. Similarly, prevent, preventing or prevention shall have the same meaning without concerning the grammar.

"Oligonucleotide": An oligonucleotide means multiple nucleotides (i.e. molecules comprising a sugar (e.g. deoxyribose) linked to a phosphate group and to an exchangeable organic base, which is either a substituted pyrimidine (Py) (e.g., cytosine (C), thymine (T)) or a substituted purine (Pu) (e.g., adenine (A) or guanine (G)). The term oligonucleotide as used herein refers to oligodeoxyribonucleotide (ODN). The oligonucleotide can be obtained from existing nucleic acid sources (e.g., genomic or cDNA), but are preferably synthetic. The oligonucleotide of the invention can be synthesized by a variety of automated nucleic acid synthesizers available in the market. These oligonucleotides are referred to as synthetic oligonucleotides.

"Chemical modification": The oligonucleotide disclosed in the invention can encompass various chemical modifications, in comparison to natural DNA, involving a phosphodiester internucleoside bridge, a ribose unit and/or a natural nucleoside base (adenine, guanine, cytosine, thymine). The modifications can occur either during or after synthesis of the oligonucleotide. During the synthesis, modified bases can be incorporated internally or on its end. After the synthesis, the modification can be carried out using the active groups (via an amino modifier, via the 3' or 5' hydroxyl groups, or via the phosphate group). The skilled person knows examples of chemical modifications. An oligonucleotide according to the invention may have one or more modifications, wherein each modification is located at a particular phosphodiester internucleoside bridge and/or at a particular ribose unit and/or at a particular natural nucleoside base position in comparison to an oligonucleotide of the same sequence, which is composed of natural DNA. The chemical modification includes "back bone modification" of the oligonucleotide of the invention. As used herein, the modified back bone of the oligonucleotide of the invention includes, but not limited to the "phosphorothioate backbone" that refers to a stabilized sugar phosphate backbone of a nucleic acid molecule in which a non-bridging phosphate oxygen is replaced by sulfur at least one internucleotide linkage. In one embodiment a non-bridging phosphate oxygen is replaced by sulfur at each and every internucleotide linkage. Other back bone modifications denote the modification with nonionic DNA analogs, such as alkyl- and aryl-phosphonates (in which the charged phosphonate oxygen is replaced by an alkyl or aryl group), phophodiester and alkylphosphotriesters, in which the charged oxygen moiety is alkylated. In other examples, the oligonucleotide can be is a phosphorothioate/phosphodiester chimera. The chemical modification also includes the base substitutions of the oligonucleotide disclosed in the invention. The substituted purines and pyrimidines can be C-5 propyne pyrimidine and 7-deaza-7-substituted purine. The substituted purines and pyrimidines include but are not limited to adenine, cytosine, guanine, and thymine, and other naturally and non-naturally occurring nucleobases. The chemical modification of the oligonucleotide of the invention further includes the modification of the bases of the oligonucleotide. A modified base is any base which is chemically distinct from the naturally occurring bases typically found in DNA such as T, C, G and A, but which share basic chemical structures with these naturally occurring bases. The oligonucleotide of the invention can be modified by using cytidine derivatives. The term "cytidine derivative" refers to a cytidine-like nucleotide (excluding cytidine) and the term "thymidine derivative" refers to a thymidine-like nucleotide (excluding thymidine). In addition, the oligonucleotides of the invention can be chemically modified by linking a diol, such as tetraethyleneglycol or hexaethyleneglycol, at either or both termini of the oligonucleotide.

"Immune-mediated disorder": An immune-mediated disorder is a disease caused by an unwanted immune response in a subject. The disorder includes autoimmune disease, graft rejection, hypersensitivity, diseases associated with the over-stimulation of host's immune system by microbes and diseases associated with TLR activation. The oligonucleotide disclosed in the invention can be used as a remedy to treat the immune-mediated disorder.

"Immune response": A response of a cells of the immune system, such as a B cell, T cell, natural killer cell, dendritic cell, neutraphil and macrophage to a stimulus. The response includes innate immune response and adaptive (specific or acquired) immune response. The adaptive (specific or acquired) immune response includes humoral immune response and cellular immune response.

"Prevent or treat immune-mediated disorder": As used herein, prevent refers to prevent the full development of an immune-mediated disorder in a subject; treat refer a therapeutic intervene in a subject so as to ameliorate a sign or symptom of, halt the progression of, or eliminate pathological condition of the immune-mediated disorder.

"Subject": As used herein, a subject refers to a human or non-human vertebrate. Non-human vertebrates are non-human primates, livestock animals and companion animals. The oligonucleotide of the invention can be administered to prevent or/and treat immune-mediated disorder in a subject.

"Autoimmune diseases": The term "autoimmune disease" refers to a disease caused by a breakdown of self-tolerance such that the adaptive and innate immune system responds to self antigens and mediates cell and tissue damage. Autoimmune diseases are frequently characterized by means of their involvement of single organ or single cell-types or involvement of multiple organs or tissue systems. Autoimmune diseases have also been referred to as "collagen," or "collagen-vascular" or "connective tissue" diseases. Autoimmune disorders are frequently associated with hypersensitivity reactions. The oligonucleotides of the invention can be useful for treating and/or preventing various types of autoimmune diseases. Specific, non-limiting examples of autoimmune disorders are systemic lupus erythematosus, insulin-dependent (type I) diabetes mellitus, inflammatory arthritis, rheumatoid arthritis, multiple sclerosis, autoimmune hepatitis, chronic aggressive hepatitis, autoimmune hemolytic anemia, autoimmune thrombocytopenia, autoimmune atrophic gastritis of pernicious anemia, autoimmune encephalomyelitis, autoimmune orchitis, acquired hemophilia, ankylosing spondylitis, antiphospholipid syndrome, Beh.cedilla.et's syndrome, cardiomyopathy, chronic inflammatory demyelinating polyneuropathy, cicatricial pemphigoid, cold agglutinin disease, polymyositisdermatomyositis, discoid lupus, sympathetic ophthalmia, essential mixed cryoglobulinemia, fibromyalgia, fibromyositis, Guillain-Barr syndrome, idiopathic pulmonary fibrosis, idiopathic thrombocytopenic purpura, IgA nephropathy, juvenile arthritis, systemic sclerosis, polyarteritis nodosa, polychondritis, dermatomyositis, primary agammaglobulinemia, primary biliary cirrhosis, hyperimmunoglobulin E, progressive systemic sclerosis, psoriasis, Reiter's syndrome, sarcoidosis, stiff-man syndrome, uveitis, vasculitis, vitiligo☐Hashimoto's thyroiditis, Goopasture's disease, pernicious anemia, Addison's disease, dermatomyositis, Sjogren's syndrome, dermatomyositis, myasthenia gravis, Grave's disease, uveitis, allergic encephalomyelitis, glomerulonephritis, and the like (N Engl J Med, Vol. 345, No. 5, Aug. 2, 2001, p 340-350). DNA or RNA released from DNA- or RNA-containing microbes could stimulate the production of autoantibody specific to self RNA- or DNA-containing complexes and consequently led to an autoimmune disease, including but not limited to SLE.

"Hypersensitivity": A hypersensitivity is referred to the disorders wherein tissue injury occurs as a result of a humoral or cell-mediated response to antigens of endogenous or exogenous origin and has been classified into four types. Type I hypersensitivity (frequently referred to as anaphylactic, immediate-type, atopic, reagenic, IgE-mediated hypersensitivity reactions or allergy) generally result from the release of pharmacologically active substances such as histamine, slow-reacting substance of anaphylaxis (SRS-A), and eosinophilic chemotactic factor (ECF) form IgE-sensitized basophils and mast cells after contact with a specific exogenous antigen. Type I hypersensitivity includes, but not limited to, allergic extrinsic asthma, seasonal allergic rhinitis and systemic anaphylaxis. Type II hypersensitivity (also referred to as cytotoxic, cytolytic complement-dependent or cell-stimulating hypersensitivity reaction) results when antibody reacts with antigenic components of cells or tissue elements or with an antigen or hapten, which has become intimately coupled to cells or tissue. Type II hypersensitivity includes, but not limited to, autoimmune hemolytic anemia, erythroblastosis fetalis and Goodpasture's disease. Type III hypersensitivity (also referred to as toxic complex, soluble complex, or immune complex hypersensitivity reactions) results from the deposition of soluble circulating antigen-antibody complexes in vessels or in tissues, with accompanying acute inflammatory reactions at the site of immune complex deposition. Type III hypersensitivity includes, but not limited to, Arthurs reaction, serum sickness, systemic lupus erythematosis, and certain types of glomerulonephritis. Type IV hypersensitivivity (frequently called cellular, cell-mediated, delayed, or tuberculin-type hypersensitivity reactions) are caused by sensitized T-lymphocytes which result from contact with a specific antigen. Type IV hypersensitivity includes, but not limited to, contact dermatitis and allograft rejection (Richard A. et al. Immunology, Fifth Edition, 2003, W.H. FREEMAN AND COMPANY).

"Diseases associated with the over-stimulation of host's immune system by microbes": Microbe invasion, if severe, sometimes can cause systemic inflammatory response in a subject, leading to diseases associated with the over-stimulation of host's immune system by microbes. The events in the development of the diseases, such as in the case of influenza A (H5N1) or bacterial infection, include the significantly elevated blood levels of tumor necrosis factor (TNF-α), interleukin 1 (IL-1), IL-6, IL-12, interferon α (IFN-α), interferon β (IFN-β), interferon γ, chemokines interferon-inducible protein 10, monocyte chemoattractant protein 1, interleukin-8, interleukin-1β, and monocyte chemoattractant protein 1. Such responses can result in cytokine-mediated lethal shock that is responsible in part for the sepsis, ARDS, and multiorgan failure observed in many patients (The Writing Committee of the World Health Organization (WHO) Consultation on Human Influenza A/H5. Avian Influenza A (H5N1) Infection in Humans. N Engl J Med 2005; 353:1374-85). The significantly elevated blood level of cytokines followed microbe infection is termed by hypercytokinemia (hypercytokinaemia) or a cytokine storm. The research suggested that patients who contract bird flu or SARS may need drugs that suppress the immune response in addition to anti-viral drugs. The oligonucleotide of the invention can be used to treat and/or prevent the diseases associated with the stimulation of host's immune system by microbes in a subject. The microbes causing the diseases includes, but not limited to, viruses, bacteria, fungi, parasites and etiological agents of Spongiform encephalopathies. The virus that cause the diseases associated with the over-stimulation of host's immune system by microbes include: SARS CoV, influenza viruses, avian flu virus HIV-1, polio viruses, hepatitis A virus; enteroviruses, human Coxsackie's viruses, rhinoviruses, echoviruses, equine encephalitis viruses, rubella viruses, dengue viruses, encephalitis viruses, yellow fever viruses, corona viruses, vesicular stomatitis viruses, rabies viruses, Ebola viruses, parainfluenza viruses, mumps virus, measles virus, respiratory syncytial virus, influenza viruses, Hantan viruses, bunga viruses, phleboviruses, Nairo viruses, hemorrhagic fever viruses; reoviruses, orbiviurses and rotaviruses, Hepatitis B virus, parvoviruses, papilloma viruses, polyoma viruses, adenoviruses, herpes simplex virus (HSV) 1 and HSV-2, varicella zoster virus, cytomegalovirus (CMV), herpes viruses, variola viruses, vaccinia viruses, pox viruses, African swine fever virus, the etiological agents of Spongiform encephalopathies, delta hepatitis virus, Hepatitis C virus, foot and mouth disease virus and avian flu virus. The bacteria that can cause the diseases associated with the over-stimulation of host's immune system by microbes include: *Helicobacter pyloris, Borelia burgdorferi, Legionella pneumophilia, Mycobacteria* sps (such as. *M. tuberculosis, M. avium,* M. E intracellulare, *M. kansaii, M. gordonae*), *Staphylococcus aureus, Neisseria gonorrhoeae, Neisseria meningitidis, Listeria monocytogenes,* Group A *Streptococcus,* Group B *Streptococcus, Streptococcus, Streptococcus faecalis, Streptococcus bovis, Streptococcus* (anaerobic sps.), *Streptococcus pneumoniae,* pathogenic *Carnpylobacter* sp., *Enterococcus* sp., *Haemophilus influenzae, Bacillus antracis, corynebacterium diphtheriae, corynebacterium* sp., *Erysipelothrix rhusiopathiae, Clostridium perfringers, Clostridium tetani, Enterobacter aerogeytes, Klebsiella pneumoniae, Pasturella multocida, Bacteroides* sp., *Fusobacterium nucleatum, Streptobacillus moniliformis, Treponema pallidium, Treponema pertenue, Leptospira,* and *Actinomyces israelli.* The fungi that can cause the diseases associated with the over-stimulation of host's immune system by microbes include, but not limited to, *Cryptococcus neoformans, Histoplasma capsulatum, Coccidioides immitis, Blastomyces dermatitidis, Chlamydia trachomatis, Candida albicans.* The parasites that can cause the diseases associated with the over-stimulation of host's immune system by microbes include: *Plasmodium falciparum* and *Toxoplasma gondii.*

"Graft rejection": The graft rejection is an immune-mediated disorder caused by organ or tissue transplantation, Transplantation means the transfer of transplants (grafts) from a donor to a recipient. Grafts are the living cells, tissues, or organs transplanted from a donor to a recipient. An autograft is the a graft transferred of one's own tissue from one location to another; a syngeneic graft (isograft) is a graft between identical twins; an allogeneic graft (homograft) is a graft between genetically dissimilar members of the same species; and a xenogeneic graft (heterograft) is a transplant between members of different species. When a subject is the recipient of an allogeneic graft or a xenogeneic graft, the body can produce an immune response against the donor tissue. In this situation, there is a clear need to suppress the immune response, in order to avoid rejection of the graft (Richard A. et al. Immunology, Fifth Edition, 2003, W.H. FREEMAN AND COMPANY). The oligonucleotides of the present invention are useful when administered for the prevention of the graft rejection. Examples of the grafts are heart, kidney, liver, medulla ossium, skin, cornea, lung, pancreas, intestinum tenue, limb, muscle, nervus, duodenum, small-bowel, pancreatic-islet-cell, and the like. In some case, the recipient may be an animals as defined in "subject" of the invention.

"Toll-like receptor (TLR)-mediated diseases": A Toll-like receptor (TLR)-mediated disease means an immune mediated disorder related to the activation of members of the TLR family. The disease includes, but not limited to, the diseases include but not limited to, sepsis associated with the activation of TLR4 by lipopolysaccharide (LPS), dilated cardiomyopathy associated with the activation of TLR2, 3, 4, 9, diabetes associated with the activation of TLR2, 3, 4, 9, experimental autoimmune encephalomyelitis associated with the activation of TLR3, systemic lupus erythematosus associated with the activation of TLR9, atherosclerosis associated with the activation of TLR4, asthma associated with the activation of TLR4 by LPS, chronic obstructive pulmonary disease associated with the activation of TLR4, EAE associated with the activation of TLR4 and organ failure associated with the activation of TLR4 (Foo Y. et al. Nature Review Immunology, Vol 5, 2005, 446-458). CpG-containing DNA (a TLR9 agonist) derived from a nucleic acid-containing infectious agent could be identified from SLE serum that induces an efficient immune response dominated by IFN-α secretion that is thought to contribute the development of SLE. The oligonucleotides of the present invention can be administered for treating and/or prevent the Toll-like receptor (TLR)-mediated diseases including but not limited to SLE in a subject.

"CpG ODN": It has been documented that TLR9 agonist activates both innate and adaptive immune response (Arthur M. Krieg. Nature Reviews Drug Discovery, Vol 5. June 2006, 471-484). CpG containing oligonucleotides (CpG ODN) is a TLR9 agonist [D. M. Klinman, Nat. Rev., Immunol. 4 (2004) 249-258]. Based on the functional characteristics, CpG ODNs are divided into three types (Tomoki Ito, et al. Blood, 2006, Vol 107, Num 6: 2423-2431). A-type CpG ODN activates human plasmacytoid dendritic cells (pDCs) to produce large amount of type I interferon (IFN-a/β) and strongly activates natural killer cells (NK cells). B-type CpG ODN primarily activates B cells, resulting in their proliferation and antibody secretion. C-type CpG ODN shares the activities of both A- and B-type CpG ODN. As a TLR9 agonist, CpG ODN such as CpG 2216 or CpG 2006 or CpG C274 can be endocytosed into a cellular compartment where they are exposed to and activate TLR9. In pDC, TLR9 activation initiate a rapid innate immune response that is characterized by the secretion of pro-inflammatory cytokines [IL-6, tumor-necrosis factor-α (TNFα)], the secretion of type I interferon (IFN) and the secretion of secretion of IFN-inducible chemokines. Through both IFN-dependent and IFN-independent pathways, innate immune cells including natural killer (NK) cells, monocytes and neutrophils are secondarily activated by the pDC. B cells activated through TLR9 have a greatly increased sensitivity to antigen stimulation and efficiently differentiate into antibody-secreting cells, and therefore contributing to the adaptive immune response, especially humoral immune response. pDC activated through TLR9 secrete IFNα, which drives the migration and clustering of pDC to lymph nodes and other secondary lymphoid tissues where the pDC activates naive and memory T cells, assists the cross-presentation of soluble protein antigens to CD8+ cytotoxic T lymphocyte (CTL) and promotes strong TH1 biased cellular CD4 and CD8 T-cell responses. Based on the above mentioned findings, it is obvious that the agents that antagonize the activity of CpG ODN can be used to treat or prevent the immune-mediated disorder by inhibiting both innate and adaptive immune response.

"Pharmaceutically acceptable carrier": A pharmaceutically acceptable carrier denotes one or more solid or liquid filler, diluents or encapsulating substances that are suitable for administering the oligonucleotide of the invention to a subject. The carrier can be organic, inorganic, natural or synthetic. The carrier includes any and all solutions, diluents, solvents, dispersion media, liposome, emulsions, coatings, antibacterial and anti-fungal agents, isotonic and absorption delaying agents, and any other carrier suitable for administering the oligonucleotide of the invention and their use is well known in the art. The pharmaceutically acceptable carriers are selected depending on the particular mode of administration of the oligonucleotide. The parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

"Therapeutically effective amount": In order to treat or prevent an immune-mediated disorder, a therapeutically effective amount of an oligonucleotide of the invention is administered to a subject. The "therapeutically effective amount" of one of the oligonucleotides means a sufficient amount of the oligonucleotide used to achieve a desired result of treating or preventing an immune-mediated disorder in a subject. The oligonucleotides of the present invention may be employed in pure form or in pharmaceutically acceptable carriers. Alternatively, the oligonucleotides may be administered as pharmaceutical compositions. The "amount" in the invention shall refer to a dose. The dose can be determined by standard techniques well known to those skilled in the art and can vary depending the factors including, but not limited to the size or/and overall health of the subject or the severity of the disease. Introduction of the oligonucleotide of the invention can be carried out as a single treatment or over a series of treatments. Subject doses of the oligonucleotide of the invention for the administration range from about 1 µg to 100 mg per administration. However, doses for the treatment of immune-mediated disorder may be used in a range of 10 to 1,000 times higher than the doses described above. The more preferable doses can be adjusted to provide the optimum therapeutic effect by those skilled in the art, for example, by the attending physician within the scope of sound medical judgment.

"Route of administration": For clinical use, the oligonucleotides of the invention can be administered alone or formulated in a pharmaceutical composition via any suitable route of administration that is effective to achieve the desired therapeutic result. The "route" of administering the oligonucleotide of the invention shall mean the enteral, parenteral and topical administration or inhalation. The enteral routes of administration of the oligonucleotide of the invention include oral, gastric, intestinal, and rectal. The parenteral route includes intravenous, intraperitoneal, intramuscular, intrathecal, subcutaneous, local injection, vaginal, topical, nasal, mucosal, and pulmonary administration. The topical route of administration of the oligonucleotide of the invention denotes the application of the oligonucleotide externally to the epidermis, to the buccal cavity and into the ear, eye and nose.

"Pharmaceutical composition": A pharmaceutical composition shall mean the composition comprising an therapeutically effective amount of the oligonucleotide of the invention with or without a pharmaceutically acceptable carrier. The pharmaceutical compositions can comprise one or more oligonucleotides of the invention. The composition includes but not limited to aqueous or saline solutions, particles, aerosols, pellets, granules, powders, tablets, coated tablets, (micro) capsules, suppositories, syrups, emulsions, suspensions, creams, drops and other pharmaceutical compositions suitable for use in a variety of drug delivery systems. The compositions may be administered parenterally, orally, rectally, intravaginally, intraperitoneally, topically (in a dosage form as powders, ointments, gels, drops or transdermal patch), bucally, or as an oral or nasal spray. In all cases, the composition must be sterile and stable under the conditions of manufacture and storage and preserved against the microbial contamination. Pharmaceutical compositions of this invention for parenteral injection comprise pharmaceutically-acceptable sterile aqueous or nonaqueous solutions, dispersions, suspensions or emulsions, as well as sterile powders for reconstitution into sterile injectable solutions or dispersions just prior to use. The oligonucleotide of the invention can be suspended in an aqueous carrier, for example, in an isotonic buffer solution at a pH of about 3.0 to about 8.0, preferably at a pH of about 3.5 to about 7.4, 3.5 to 6.0, or 3.5 to about 5.0. The buffer solution includes sodium citrate-citric acid and sodium phosphate-phosphoric acid, and sodium acetate-acetic acid buffers. For oral administration, the composition will be formulated with edible carriers to form powders tablets, pills, dragees, capsules, liquids, gels, syrups, slurries, suspensions and the like. For solid compositions, conventional non-toxic solid carriers can include pharmaceutical grades of mannitol, lactose, starch, or magnesium stearate. For buccal administration, the composition will be tablets or lozenges in conventional manner. For inhalation, the composition will be an aerosol spray from pressurized packs or a nebulizer or a dry powder and can be selected by one of skill in the art. In some cases, in order to prolong the effect of the oligonucleotide of the invention, the oligonucleotides of the invention are also suitably administered by sustained-release systems. The oligonucleotide of the invention can be used in a liquid suspension of crystalline or amorphous material with poor water solubility to slow the releasing of the oligonucleotide. Alternatively, delayed releasing of a parenterally administered drug form of the oligonucleotide is accomplished by dissolving or suspending the oligonucleotide in hydrophobic materials (such as an acceptable oil vehicle). Injectable depot forms are made by entrapping the oligonucleotide in liposomes or microemulsions or other biodegradable semi-permeable polymer matrices such as polylactide-polyglycolide, poly (orthoesters) and poly (anhydrides).

"Active ingredients": The oligonucleotides of the invention can be used alone, in combination with themselves, in a pharmaceutically acceptable carrier, in combination with one or more additional active ingredients. The administration of the oligonucleotide of the invention and additional active ingredients can be sequential or simultaneous. The active ingredients include non-steroidal anti-inflammatory agents, steroids, nonspecific immunosuppressive agent, biological response modifier, chemical compound, small molecule, nucleic acid molecule and TLR antagonists. The active ingredients also denote the agents that suppress the immune activation by antagonizing chemochines, by inducing the generation of regulatory T cells (CD4+CD25+ T cells), by inhibiting a complement, matrix metalloproteases and nitric oxide synthase, by blocking costimulatory factors and by inhibiting the signaling cascades in the immune cells. The non-steroidal anti-inflammatory agents include, but unlimited to, diclofenac, diflunisal, etodolac, flurbiprofen, ibuprofen, indomethacin, ketoprofen, ketorolac, nabumetone, naproxen, oxaprozin, piroxicam, sulindac, tohnetin, celecoxib and rofecoxib. The steroids include, but unlimited to, cortisone, dexamethasone, hydrocortisone, methylprednisolone, prednisolone, prednisone, and triamcinolone. A nonspecific immunosuppressive agent means the agent used to prevent the development of immune-mediated disorder. The nonspecific immunosuppressive agents include but not limited to cyclophosphamide, cyclosporine, methotrexate, steroids, FK506, tacrolimus, mycophenolic acid and sirolimus. The biological response modifier includes a recombinant interleukin-1-receptor antagonist (Kineret or anakima), a soluble p75 TNF-a receptor-IgG1 fusion protein (etanercept or Enbrel), or a monoclonal antibody against TNF-a (infliximab or RemicadeX). The agents also include Interferon beta-1a, interleukin-10 and TGFβ.

"Delivery vehicle": The oligonucleotides of the invention can be administered in/with a delivery vehicle or in a form linked with a vehicle. The vehicle includes, but not limited to, sterol (e.g., cholesterol), cochleates, emulsomes, ISCOMs; a lipid (e.g., a cationic lipid, anionic lipid), liposomes; ethylene glycol (PEG); live bacterial vectors (e.g., *Salmonella, Escherichia coli, bacillus* Calmette-Gurin, *Shigella, Lactobacillus*), live viral vectors (e.g., Vaccinia, adenovirus, Herpes simplex), virosomes, virus-like particles, microspheres, nucleic acid vaccines, polymers (e.g., carboxymethylcellulose, chitosan), polymer rings and a targeting agent that recognizes target cell by specific receptors.

"Pegylation": Pegylation is the process of covalent attachment of poly (ethylene glycol) polymer chains to another molecule, normally a drug or therapeutic protein. Pegylation is routinely achieved by incubation of a reactive derivative of PEG with the target agent. The pegylated agent can "mask" the agent from the host's immune system, increase the hydrodynamic size of the agent which prolongs its circulatory time. The oligonucleotides of the invention can be pegylated.

We claim:

1. A method for treating a TLR7 or TLR9 activation-associated disorder in a subject comprising administrating the subject an effective amount of a single-stranded oligonucleotide with the sequence 5'-cctcctcctcctcctcctcctcct-3' (SEQ ID NO: 1).

2. The method of claim 1, wherein the disorder is TLR9 activation-associated disorder.

3. The method of claim 1, wherein the subject is a human or non-human vertebrate.

4. The method of claim 1, wherein the treatment of the TLR7 or TLR9 activation-associated disorder is carried out by a mechanism selected from the group comprising inhibiting the proliferation of immune cells activated with Toll like receptor 9 agonist, inhibiting the activation of Toll like receptor 9, inhibiting interferon production, and rescuing a subject from cytokine-mediated lethal shock.

5. The method of claim 1, wherein the TLR7 or TLR9 activation-associated disorder is systemic lupus erythematosus (SLE), rheumatoid arthritis, or multiple organ dysfunction syndromes.

6. The method of claim 1, wherein the oligonucleotide is administered enterally, parenterally, topically, or inhalationally.

7. The method of claim 1, wherein the oligonucleotide comprises one or more chemical modifications.

8. The method of claim 1, the oligonucleotide comprises one or more internucleoside phosphorothioate bonds.

9. The method of claim 1, wherein the oligonucleotide is pegylated.

10. A method for treating or preventing systemic lupus erythematosus (SLE) in a subject comprising administering to the subject an effective amount of a single-stranded oligonucleotide with the sequence 5'-cctcctcctcctcctcctcctcct-3' (SEQ ID NO: 1).

11. The method of claim 10 wherein the subject is a human or non-human vertebrate.

12. The method of claim 10 wherein the oligonucleotide is administered enterally, parenterally, topically, or inhalationally.

13. The method of claim 10, wherein the oligonucleotide comprises one or more chemical modifications.

14. The method of claim 10, the oligonucleotide comprises one or more internucleoside phosphorothioate bonds.

15. The method of claim 10, wherein the oligonucleotide is pegylated.

16. The method of claim 10, wherein the disorder is TLR9 activation-associated disorder.

* * * * *

SEQUENCE LISTING

```
<160> NUMBER OF SEQ ID NOS: 8

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cctcctcctc ctcctcctcc tcct                                            24

<210> SEQ ID NO 2
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: This sequence may encompass 2-50 "cct"
      repeating units

<400> SEQUENCE: 2
cctcctcctc ctcctcctcc tcctcctcct cctcctcctc ctcctcctcc tcctcctcct    60
cctcctcctc ctcctcctcc tcctcctcct cctcctcctc ctcctcctcc tcctcctcct   120
cctcctcctc ctcctcctcc tcctcctcct                                    150

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tcgtcgtttt gtcgttttgt cgtt                                            24

<210> SEQ ID NO 4
<211> LENGTH: 21
<212> TYPE: DNA
<213> ORGANISM: Artificial Sequence
<220> FEATURE:
```

-continued

```
<223> OTHER INFORMATION: Description of Artificial Sequence: Synthetic
      oligonucleotide

<400> SEQUENCE: 4
tcgtcgaacg ttcgagatga t                                             21

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ttagggttag ggttagggtt aggg                                          24

<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gttagagatt aggca                                                    15

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
aaaaataaaa ataaaataaa at                                            22

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tccatgacgt tcctgacgtt                                               20
```